United States Patent
Kaloshian et al.

(10) Patent No.: US 10,738,322 B2
(45) Date of Patent: Aug. 11, 2020

(54) NEGATIVE REGULATOR OF PLANT IMMUNITY AGAINST NEMATODES

(71) Applicant: The Regents of the University of California, Oakland, CA (US)

(72) Inventors: Isgouhi Kaloshian, Riverside, CA (US); Marcella Alves Teixeira, Brasilia (BR)

(73) Assignee: The Regents of the University of California, Oakland, CA (US)

( * ) Notice: Subject to any disclaimer, the term of this patent is extended or adjusted under 35 U.S.C. 154(b) by 125 days.

(21) Appl. No.: 15/799,191

(22) Filed: Oct. 31, 2017

(65) Prior Publication Data

US 2018/0119168 A1 May 3, 2018

Related U.S. Application Data

(60) Provisional application No. 62/417,078, filed on Nov. 3, 2016.

(51) Int. Cl.

| | |
|---|---|
| *C12N 15/82* | (2006.01) |
| *C12N 9/22* | (2006.01) |
| *C12N 15/11* | (2006.01) |
| *C12N 15/113* | (2010.01) |

(52) U.S. Cl.
CPC .......... *C12N 15/8285* (2013.01); *C12N 9/22* (2013.01); *C12N 15/11* (2013.01); *C12N 15/1137* (2013.01); *C12N 15/8216* (2013.01); *C12N 15/8218* (2013.01); *C12N 2310/14* (2013.01); *C12N 2310/20* (2017.05); *Y02A 40/164* (2018.01)

(58) Field of Classification Search
None
See application file for complete search history.

(56) References Cited

U.S. PATENT DOCUMENTS

| | | | |
|---|---|---|---|
| 10,316,325 B1 * | 6/2019 | Creelman | .......... C12N 15/8227 |
| 2009/0158454 A1 | 6/2009 | Allen et al. | |
| 2013/0091598 A1 | 4/2013 | Wiig et al. | |

FOREIGN PATENT DOCUMENTS

WO   2014/112875 A1   7/2014

OTHER PUBLICATIONS

Teixeira, Marcella Alves. Root-Knot Nematode-Triggered Defense Responses in *Arabidopsis thaliana* during Early Stages of Parasitism. University of California, Riverside, 2017 (Year: 2017).*
Teixeira, Marcella A., et al. "Classification and phylogenetic analyses of the *Arabidopsis* and tomato G-type lectin receptor kinases." BMC genomics 19.1 (2018): 239. (Year: 2018).*
Desclos-Theveniau, Marie, et al. "The Arabidopsis lectin receptor kinase LecRK-V. 5 represses stomatal immunity induced by Pseudomonas syringae pv. tomato DC3000." PLoS pathogens 8.2 (2012). Included in IDS Mar. 24, 2020 (Year: 2012).*
GLYMA18G40290 Submission; Available online at http://www.pantherdb.org/genes/gene.do?acc=Soybn%7CEnsemblGenome=GLY MA18G40290%7CUniProtKB=I1N2K7, in entirety; protein ID No. I1N2K7; Organism: Glycine max; Oct. 5, 2016; 5 pages.
De Schutter et al., Protein-Carbohydrate Interactions as Part of Plant Defense and Animal Immunity, Molecules, vol. 20, May 19, 2015, pp. 9029-9053.
Desclos-Theveniau et al., the Arabidopsis Lectin Receptor Kinase LecRK-V.5 Represses Stomatal Immunity Induced by Pseudomonas syringae pv. tomato DC3000, PLoS Pathogens, vol. 8, Issue 2, 9 Feb. 2012, pp. 1-12.
Singh et al., Lectin receptor kinases in plant innate immunity, Frontiers in Plant Science, vol. 4, 7 May 2013, Article 124, pp. 1-4.
Singh et al., the Lectin Receptor Kinase-Vi.2 Is Required for Priming and Positively Regulates Arabidopsis Pattern-Triggered Immunity, the Plant Cell, vol. 24, Mar. 2012, pp. 1256-1270.
Vaid et al., Knights in Action: Lectin Receptor-Like Kinases in Plant Development and Stress Responses, Molecular Plant, vol. 6, No. 5, Sep. 2013, pp. 1405-1418.
Wang et al., L-type lectin receptor kinases in Nicotiana benthamiana and tomato and their role in Phytophthora resistance, Journal of Experimental Botany, 5 Aug. 2015, pp. 1-13.
Wang et al., Ectopic expression of Arabidopsis L-type lectin receptor kinase genes LecRK-I.9 and LecRK-Ix.1 in Nicotiana benthamiana confers Phytophthora resistance, Plant Cell Rep, vol. 35, 21 Jan. 2016, pp. 845-855.
Wang et al., Phenotypic Analyses of Arabidopsis T-Dna Insertion Lines and Expression Profiling Reveal That Multiple L-Type Lectin Receptor Kinases Are Involved in Plant Immunity, Molecular Plant-Microbe Interactions, vol. 27, No. 12, 2014, pp. 1390-1402.

* cited by examiner

*Primary Examiner* — Weihua Fan
(74) *Attorney, Agent, or Firm* — Kilpatrick Townsend & Stockton LLP

(57) ABSTRACT

The present invention provides methods of enhancing immunity to root knot nematodes in plants. The methods comprise introducing mutations into a G-LecRK-VI.13 gene or suppressing its expression in plants.

20 Claims, 5 Drawing Sheets

Specification includes a Sequence Listing.

a)

b)

NEGATIVE REGULATOR OF PLANT IMMUNITY AGAINST NEMATODES

CROSS REFERENCE TO RELATED APPLICATIONS

This application claims priority to U.S. Provisional Application No. 62/417,078, filed on Nov. 3, 2016, the contents of which are incorporated by reference herewith in their entirety.

REFERENCE TO A "SEQUENCE LISTING" SUBMITTED AS ASCII TEXT FILES VIA EFS-WEB

The Sequence Listing written in file 081906-224210US-1064032_SequenceListing.txt created on Oct. 26, 2017, 31,689 bytes, machine format IBM-PC, MS-Windows operating system, in accordance with 37 C.F.R. §§ 1.821- to 1.825, is hereby incorporated by reference in its entirety for all purposes.

BRIEF SUMMARY OF THE INVENTION

The present invention provides methods of making a plant which has an enhanced immune response to root knot nematodes (members of the genus *Meloidogyne*). The methods comprise introducing into a parent plant a recombinant construct that specifically inhibits activity of G-LecRK-VI.13 in the plant. Progeny of the parent plant which have an enhanced immune response to nematodes are selected.

In some embodiments, the methods of the invention comprise (a) introducing into a parent plant a recombinant construct encoding an genome editing protein that specifically introduces mutations into the G-LecRK-VI.13 gene; and (b) selecting progeny of the parent plant comprising a mutant G-LecRK-VI.13 gene and has an enhanced immune response to nematodes. The recombinant construct can encode an endonuclease (e.g., a cas9 endonuclease) and a guide RNA molecule that specifically targets the endonuclease to the G-LecRK-VI.13 gene. The G-LecRK-VI.13 gene may be at least about 90% identical to SEQ ID NO: 1, 3, or 5.

In other embodiments, the methods comprise a) introducing into a parent plant a recombinant construct that specifically inhibits expression of the G-LecRK-VI.13 gene; and b) selecting progeny of the parent plant having an enhanced immune response to nematodes. The recombinant construct may comprise a nucleic acid sequence encoding a microRNA or an siRNA specific to the G-LecRK-VI.13 gene. The G-LecRK-VI.13 gene may be at least about 90% identical to SEQ ID NO: 1, 3, or 5.

The invention also provides plants made by the methods of the invention. The plant may be rice, peanut, or tomato.

The invention further provides recombinant constructs used in the methods of the invention.

DETAILED DESCRIPTION OF THE INVENTION

Definitions

Figure 1:
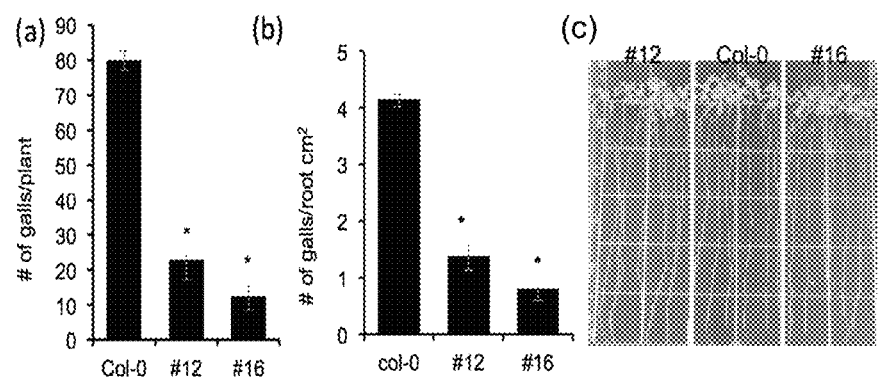
FIG. 1. AT1G61550 is involved in RKN resistance. (a) Number of galls/plant and (b) number of galls/cm2 of root, measured by Image J, of two T-DNA insertion lines of AT1G61550 (#12 & #16). n=90. Each seedling was inoculated with 100 RKN infective stage juveniles. Data are from 3 independent experiments. P<0.001. (c) Seedlings growing on agar media in plates.

The term "plant" includes whole plants, shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

The invention has use over a broad range of agronomically important species including species from the genera *Arachis, Asparagus, Atropa, Aven, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malta, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna*, and *Zea*.

The term "progeny" refers generally to the offspring of selfing or a cross and includes direct first generation progeny (e.g., F1), as well as later generations (e.g., F2, F3, etc).

As used herein, "transgenic plant" includes reference to a plant that comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid, including those transgenics initially so altered as well as those created by sexual crosses or asexual propagation from the initial transgenic.

A "non-transgenic plant" is a plant that lacks a heterologous polynucleotide stably integrated into its genome. Such a plant may comprise alterations of its genome (chromosomal or extra-chromosomal) that are introduced by the methods of the invention, conventional plant breeding methods or by naturally occurring events such as random cross-fertilization, non-recombinant viral infection, non-recombinant bacterial transformation, non-recombinant transposition, or spontaneous mutation.

The term "expression cassette" refers to any recombinant expression system for the purpose of expressing a nucleic acid sequence of the invention in vitro or in vivo, constitutively or inducibly, in any cell, including, in addition to plant cells, prokaryotic, yeast, fungal, insect or mammalian cells. The term includes linear and circular expression systems. The term includes all vectors. The cassettes can remain episomal or integrate into the host cell genome. The expression cassettes can have the ability to self-replicate or not (i.e., drive only transient expression in a cell). The term includes recombinant expression cassettes that contain only the minimum elements needed for transcription of the recombinant nucleic acid.

The term "constitutive" or "constitutively" denotes temporal and spatial expression of the polypeptides of the present invention in plants in the methods according to various exemplary embodiments of the invention. The term "constitutive" or "constitutively" means the expression of the polypeptides of the present invention in the tissues of the plant throughout the life of the plant and in particular during its entire vegetative cycle. In some embodiments, the polypeptides of the present invention are expressed constitutively in all plant tissues. In some embodiments, the polypeptides of the present invention are expressed constitutively in the roots, the leaves, the stems, the flowers, and/or the fruits. In other embodiments of the invention, the polypeptides of the present invention are expressed constitutively in the roots, the leaves, and/or the stems.

The term "inducible" or "inducibly" means the polypeptides of the present invention are not expressed, or are expressed at very low levels, in the absence of an inducing agent. The expression of the polypeptides of the present invention is greatly induced in response to an inducing agent.

The term "inducing agent" is used to refer to a chemical, biological or physical agent or environmental condition that effects transcription from an inducible regulatory element. In response to exposure to an inducing agent, transcription from the inducible regulatory element generally is initiated de novo or is increased above a basal or constitutive level of expression. Such induction can be identified using the methods disclosed herein, including detecting an increased level of RNA transcribed from a nucleotide sequence operatively linked to the regulatory element, increased expression of a polypeptide encoded by the nucleotide sequence, or a phenotype conferred by expression of the encoded polypeptide.

A "LecRK-VI.13 gene" or a "LecRK-VI.13 polynucleotide" is a gene or nucleic acid sequence (DNA or RNA) comprising at least a portion of a coding region which encodes a LecRK-VI.13 protein of the invention. A LecRK-VI.13 polynucleotide may also be an RNA molecule (e.g., short intefering RNA, or microRNA) transcribed from a LecRK-VI.13 DNA. In some embodiments, the LecRK-VI.13 polynucleotide may comprise a coding sequence at least substantially identical (e.g., at least 80% identical) to AT1G61550 (SEQ ID NO:1), Solyc04g058110 (SEQ ID NO: 3), or Solyc04g008400.A (SEQ ID NO: 5). Other LecRK-VI.13 genes include LOC_Os07g36590.1, Aradu.AX3Z0, Solyc03g006720, Solyc03g006730.A, and Solyc03g006730.B.

A "LecRK-VI.13 polypeptide" or "LecRK-VI.13 protein" is a polypeptide or protein which is at least substantially identical to any polypeptide sequence encoded by the polynucleotides noted above and which modulates root knot nematode immunity in plants. LecRK-VI.13 polypeptide or protein can also be identified by the presence of one or more of the domains discussed below.

The phrase "substantially identical," in the context of the present invention refers to polynucleotides or polypeptides that have sufficient sequence identity with a reference sequence (e.g., SEQ ID No: 1, 3, or 5) to effect similar functionality when expressed in plants as the reference sequence. In accordance with one aspect of an exemplary embodiment of the invention, a polynucleotide or a polypeptide that exhibits at least 80% sequence identity with a reference sequence may be deemed to be "substantially identical;" however, polynucleotides and polypeptides that exhibit less (even significantly less, e.g., 60%-70% or less) than 80% sequence identity may, in accordance with various exemplary embodiments of the invention, be "substantially identical" to their reference sequences if requisite functionality is achieved. Alternatively, percent identity can be any value from 90% to 100%. More preferred embodiments include at least: 80%, 85%, 90%, 95%, or 99% identity as used herein is as compared to the reference sequence using the programs described herein; preferably BLAST using standard parameters, as described below.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions, such as from 20 to 600, usually about 50 to about 200, more usually about 100 to about 150, in which a sequence may be compared to a reference sequence of the same number of contiguous positions after the two sequences are optimally aligned. If no range is provided, the comparison window is the entire length of the reference sequence. Methods of alignment of sequences for comparison are well-known in the art. Optimal alignment of sequences for comparison can be conducted e.g., by the local homology algorithm of Smith and Waterman, *Adv. Appl. Math.* 2:482, 1981; by the homology alignment algorithm of Needleman and Wunsch, *J. Mol. Biol.* 48:443, 1970; by the search for similarity method of Pearson and Lipman, *Proc. Nat'l. Acad. Sci. USA* 85:2444, 1988; by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

An example of an algorithm that is suitable for determining percent sequence identity and sequence similarity is the BLAST algorithm, which is described in Altschul, S. F. et al., *J. Mol. Biol.* 215:403-410, 1990. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, S. F. et al., supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff, *Proc. Natl. Acad. Sci. USA* 89:10915, 1989), alignments (B) of 50, expectation (E) of 10, M=5, N=−4, and a comparison of both strands.

The BLAST algorithm also performs a statistical analysis of the similarity between two sequences (see, e.g., Karlin and Altschul, *Proc. Nat'l. Acad. Sci. USA* 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, preferably less than about 0.01, and more preferably less than about 0.001.

Genome Editing Proteins

Any of a number of genome editing proteins well known to those of skill in the art can be used in the methods of the invention. The particular genome editing protein used is not critical, so long as it provides site-specific mutation of a desired nucleic acid sequence. Exemplary genome editing proteins include targeted nucleases such as engineered zinc finger nucleases (ZFNs), transcription-activator like effector nucleases (TALENs), and engineered meganucleases. In addition, systems which rely on an engineered guide RNA (a gRNA) to guide an endonuclease to a target cleavage site can be used. The most commonly used of these systems is the CRISPR/Cas system with an engineered guide RNA to guide the Cas-9 endonuclease to the target cleavage site.

CRISPR (Clustered Regularly Interspaced Short Palindromic Repeats)/Cas (CRISPR-associated) system, are adaptive defense systems in prokaryotic organisms that cleave foreign DNA. CRISPR loci in microbial hosts contain a combination of CRISPR-associated (Cas) genes as well as non-coding RNA elements which determine the specificity of the CRISPR-mediated nucleic acid cleavage. Three types (I-III) of CRISPR systems have been identified across a wide range of bacterial hosts. In the typical system, a Cas endonuclease (e.g., Cas9) is guided to a desired site in the genome using small RNAs that target sequence-specific single- or double-stranded DNA sequences. The CRISPR/Cas system has been used to induce site-specific mutations in plants (see Miao et al. 2013 *Cell Research* 23:1233-1236).

The basic CRISPR system uses two non-coding guide RNAs (crRNA and tracrRNA) which form a crRNA:tracrRNA complex that directs the nuclease to the target DNA via Wastson-Crick base-pairing between the crRNA and the target DNA. Thus, the guide RNAs can be modified to recognize any desired target DNA sequence. More recently, it has been shown that a Cas nuclease can be targeted to the target gene location with a chimeric single-guide RNA (sgRNA) that contains both the crRNA and tracRNA elements. It has been shown that Cas9 can be targeted to desired gene locations in a variety of organisms with a chimeric sgRNA (Cong et al. 2013 *Science* 339:819-23).

Zinc finger nucleases (ZFNs) are engineered proteins comprising a zinc finger DNA-binding domain fused to a nucleic acid cleavage domain, e.g., a nuclease. The zinc finger binding domains provide specificity and can be engineered to specifically recognize any desired target DNA sequence. For a review of the construction and use of ZFNs in plants and other organisms, see Urnov et al. 2010 *Nat Rev Genet*. 11(9):636-46.

Transcription activator like effectors (TALEs) are proteins secreted by certain species of *Xanthomonas* to modulate gene expression in host plants and to facilitate bacterial colonization and survival. TALEs act as transcription factors and modulate expression of resistance genes in the plants. Recent studies of TALEs have revealed the code linking the repetitive region of TALEs with their target DNA-binding sites. TALEs comprise a highly conserved and repetitive region consisting of tandem repeats of mostly 33 or 34 amino acid segments. The repeat monomers differ from each other mainly at amino acid positions 12 and 13. A strong correlation between unique pairs of amino acids at positions 12 and 13 and the corresponding nucleotide in the TALE-binding site have been found. The simple relationship between amino acid sequence and DNA recognition of the TALE binding domain allows for the design DNA binding domains of any desired specificity.

TALEs can be linked to a non-specific DNA cleavage domain to prepare genome editing proteins, referred to as TALENs. As in the case of ZFNs, a restriction endonuclease, such as FokI, can be conveniently used. For a description of the use of TALENs in plants, see Mahfouz et al. 2011 *Proc Natl Acad Sci USA*. 108:2623-8 and Mahfouz 2011 *GM Crops*. 2:99-103.

Meganucleases are endonucleases that have a recognition site of 12 to 40 base pairs. As a result, the recognition site occurs rarely in any given genome. By modifying the recognition sequence through protein engineering, the targeted sequence can be changed and the nuclease can be used to cleave a desired target sequence. (See Seligman, et al. 2002 *Nucleic Acids Research* 30: 3870-9 WO06097853, WO06097784, WO04067736, or US20070117128).

In addition to the methods described above, other methods for introducing genetic mutations into plant genes and selecting plants with desired traits are known. For instance, seeds or other plant material can be treated with a mutagenic chemical substance, according to standard techniques. Such chemical substances include, diethyl sulfate, ethylene imine, ethyl methanesulfonate (EMS) and N-nitroso-N-ethylurea. Alternatively, ionizing radiation from sources such as, X-rays or gamma rays can be used.

Suppression of LecRK-VI.13 Expression

The invention also provides methods of suppressing LECRK-VI.13 expression or activity in a plant using expression cassettes that transcribe LECRK-VI.13 RNA molecules that inhibit endogenous LECRK-VI.13 expression or activity in a plant cell. Suppressing or silencing gene function refers generally to the suppression of levels of LECRK-VI.13 mRNA or LECRK-VI.13 protein expressed by the endogenous LECRK-VI.13 gene and/or the level of the LECRK-VI.13 protein functionality in a cell. The terms do not specify mechanism and could include RNAi (e.g., short interfering RNA (siRNA) and micro RNA (miRNA)), antisense, cosuppression, viral-suppression, hairpin suppression, stem-loop suppression, and the like.

A number of methods can be used to suppress or silence gene expression in a plant. The ability to suppress gene function in a variety of organisms, including plants, using double stranded RNA is well known. Expression cassettes encoding RNAi typically comprise a polynucleotide sequence at least substantially identical to the target gene linked to a complementary polynucleotide sequence. The sequence and its complement are often connected through a linker sequence that allows the transcribed RNA molecule to fold over such that the two sequences hybridize to each other.

RNAi (e.g., siRNA, miRNA) appears to function by base-pairing to complementary RNA or DNA target sequences. When bound to RNA, the inhibitory RNA molecules trigger either RNA cleavage or translational inhibition of the target sequence. When bound to DNA target sequences, it is thought that inhibitory RNAs can mediate DNA methylation of the target sequence. The consequence of these events, regardless of the specific mechanism, is that gene expression is inhibited.

MicroRNAs (miRNAs) are noncoding RNAs of about 19 to about 24 nucleotides in length that are processed from longer precursor transcripts that form stable hairpin structures.

In addition, antisense technology can be conveniently used. To accomplish this, a nucleic acid segment at least substantially identical to the desired gene is cloned and operably linked to a promoter such that the antisense strand of RNA will be transcribed. The expression cassette is then transformed into a plant and the antisense strand of RNA is produced. In plant cells, it has been suggested that antisense RNA inhibits gene expression by preventing the accumulation of mRNA which encodes the protein of interest.

Another method of suppression is sense suppression. Introduction of expression cassettes in which a nucleic acid is configured in the sense orientation with respect to the promoter has been shown to be an effective means by which to block the transcription of target genes.

For these techniques, the introduced sequence in the expression cassette need not have absolute identity to the target gene. In addition, the sequence need not be full length, relative to either the primary transcription product or fully processed mRNA. One of skill in the art will also recognize that using these technologies families of genes can be suppressed with a transcript. For instance, if a transcript is designed to have a sequence that is conserved among a family of genes, then multiple members of a gene family can be suppressed. Conversely, if the goal is to only suppress one member of a homologous gene family, then the transcript should be targeted to sequences with the most variance between family members.

Gene expression can also be inactivated using recombinant DNA techniques by transforming plant cells with constructs comprising transposons or T-DNA sequences. Mutants prepared by these methods are identified according to standard techniques. For instance, mutants can be detected by PCR or by detecting the presence or absence of LECRK-VI.13 mRNA, e.g., by northern blots or reverse transcription PCR (RT-PCR).

Catalytic RNA molecules or ribozymes can also be used to inhibit expression of embryo-specific genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA cleaving activity upon them, thereby increasing the activity of the constructs. The design and use of target RNA-specific ribozymes is well known.

Introduction of Recombinant Constructs into Plant Cells

The recombinant construct encoding a genome editing protein or a nucleic acid that suppresses LECRK-VI.13 expression may be introduced into the plant cell using standard genetic engineering techniques, well known to those of skill in the art. In the typical embodiment, recombinant expression cassettes can be prepared according to well-known techniques. In the case of CRISPR/Cas nuclease, the expression cassette may transcribe the guide RNA, as well.

Such plant expression cassettes typically contain the polynucleotide operably linked to a promoter (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A number of promoters can be used in the practice of the invention. A plant promoter fragment can be employed which will direct expression of the desired polynucleotide in all tissues of a plant. Such promoters are referred to herein as "constitutive" promoters and are active under most environmental conditions and state of development or cell differentiation. Examples of constitutive promoters include the cauliflower mosaic virus (CaMV) 35S transcription initiation region.

Alternatively, the plant promoter can direct expression of the polynucleotide under environmental control. Such promoters are referred to here as "inducible" promoters. Environmental conditions that may affect transcription by inducible promoters include biotic stress, abiotic stress, saline stress, drought stress, pathogen attack (e.g., nematodes), anaerobic conditions, cold stress, heat stress, hypoxia stress, or the presence of light.

In addition, chemically inducible promoters can be used. Examples include those that are induced by benzyl sulfonamide, tetracycline, abscisic acid, dexamethasone, ethanol or cyclohexenol.

Examples of promoters under developmental control include promoters that initiate transcription only, or preferentially, in certain tissues such as leaves, roots, fruit, seeds, or flowers. These promoters are sometimes called tissue-preferred promoters. The operation of a promoter may also vary depending on its location in the genome. Thus, a developmentally regulated promoter may become fully or partially constitutive in certain locations. A developmentally regulated promoter can also be modified, if necessary, for weak expression.

Methods for transformation of plant cells are well known in the art, and the selection of the most appropriate transformation technique for a particular embodiment of the invention may be determined by the practitioner. Suitable methods may include electroporation of plant protoplasts, liposome-mediated transformation, polyethylene glycol (PEG) mediated transformation, transformation using viruses, micro-injection of plant cells, micro-projectile bombardment of plant cells, and *Agrobacterium tumeficiens* mediated transformation. Transformation means introducing a nucleotide sequence in a plant in a manner to cause stable or transient expression of the sequence.

In some embodiments of the invention, in planta transformation techniques (e.g., vacuum-infiltration, floral spraying or floral dip procedures) are used to introduce the expression cassettes of the invention (typically in an *Agrobacterium* vector) into meristematic or germline cells of a whole plant. Such methods provide a simple and reliable method of obtaining transformants at high efficiency while avoiding the use of tissue culture. (see, e.g., Bechtold et al. 1993 *C.R. Acad. Sci.* 316:1194-1199; Chung et al. 2000 *Transgenic Res.* 9:471-476; Clough et al. 1998 *Plant J.* 16:735-743; and Desfeux et al. 2000 *Plant Physiol* 123:895-904). In these embodiments, seed produced by the plant comprise the expression cassettes encoding the genome editing proteins of the invention. The seed can be selected based on the ability to germinate under conditions that inhibit germination of the untransformed seed.

If transformation techniques require use of tissue culture, transformed cells may be regenerated into plants in accordance with techniques well known to those of skill in the art. The regenerated plants may then be grown, and crossed with the same or different plant varieties using traditional breeding techniques to produce seed, which are then selected under the appropriate conditions.

The expression cassette can be integrated into the genome of the plant cells, in which case subsequent generations will express the encoded proteins. Alternatively, the expression cassette is not integrated into the genome of the plants cell, in which case the encoded protein is transiently expressed in the transformed cells and is not expressed in subsequent generations.

In some embodiments, the genome editing protein itself, is introduced into the plant cell. In these embodiments, the introduced genome editing protein is provided in sufficient quantity to modify the cell but does not persist after a contemplated period of time has passed or after one or more cell divisions. In such embodiments, no further steps are needed to remove or segregate away the genome editing protein and the modified cell.

In these embodiments, the genome editing protein is prepared in vitro prior to introduction to a plant cell using well known recombinant expression systems (bacterial expression, in vitro translation, yeast cells, insect cells and the like). After expression, the protein is isolated, refolded if needed, purified and optionally treated to remove any purification tags, such as a His-tag. Once crude, partially purified, or more completely purified genome editing proteins are obtained, they may be introduced to a plant cell via electroporation, by bombardment with protein coated particles, by chemical transfection or by some other means of transport across a cell membrane.

EXAMPLES

The following examples are offered to illustrate, but not to limit the claimed invention.

Identification of a Negative Regulator of Root-Knot Nematode Immunity

BAK1 is a member of the somatic embryogenesis receptor kinases (SERKs) which encodes a membrane localized leucine-rich repeat (LRR) kinase. BAK1 is a co-receptor for pattern recognition receptors (PRRs) and is required for pattern-triggered immunity (PTI) induced by several microbe-associated molecular patterns (MAMP). We identified that a bak1 mutant is involved in resistance to root-knot nematodes (RKN) (Teixeira et al, 2016 Root-knot nematodes induce pattern-triggered immunity in *Arabidopsis thaliana* roots. New Phytologist 211: 279-287). To understand the BAK1-dependent immune response to RKN and identify receptors involved in RKN recognition, we performed RNA-Seq gene expression analysis of the wild-type Col-0 and bak1 mutant infected with RKN and controls. Among the RKN regulated genes, we identified genes encoding membrane localized receptor kinases. To functionally characterize these genes, we screened their mutants with RKN. In this process, we identified two AT1G61550 [SALK_128729 (#12) and SAIL_63_G02 (#16)] mutants that displayed enhanced resistance to RKN infection as measured by the number of egg masses (the nematode reproductive structure) on infected roots (FIGS. 1a and 1b). Phenotypically, both mutant lines 12 and 16 have similar root and shoot phenotypes as the wild type Col-0 (FIG. 1c).

The At1g61550 gene and cDNA are comprised of 3,629 bp and 2,982 bp, respectively. The gene has eight introns. The predicted coding region (CDS) is 2,409 bp. At1g61550 is a member of lectin receptor kinases (LecRK). LecRKs contain extracellular lectin motifs known to bind to various carbohydrates. They are presumably localized to the plasma membrane and can contain one of three kinds of extracellular lectin motifs, G, C and L types which defines the three subgroups of this family. At1g61550 belongs to G-type LecRKs that we designated as G-LecRK-VI.13 based on phylogenetic analysis.

Both AT1G61550/G-LecRK-VI.13 mutant lines 12 and 16 are T-DNA mutants with insertions in intron 1 (before the ATG) and intron 7, respectively. Consequently, mutant line 12 is a null mutant while line 16 has a truncated transcript with a premature stop as determined by bioinformatics and qRT-PCR analyses.

Figure 2:
FIG. 2. Model for domain architecture of the G-type LecRK with EGF domain. AT1G61550/G-LecRK-VI.13 has this structure. SLG=S-locus glycoprotein, EGF=epidermal growth factor-like motif, PAN=plasminogen-apple-nematode motif; TM=transmembrane. S-domain includes: B-type lectin+SLG+PAN.

The G-lectins are characterized by the S-domain which includes three subdomains which are: the B-lectin domain and S-locus glycoprotein domain and the PAN domain (FIG. 2) (Xing et al., 2013). In addition to the S-domain, in *Arabidopsis* a subset contains one additional motif, the EGF (for Epidermal growth factor) (Xing et al., 2013). The presence of the EGF domain suggests involvement in formation of disulfide bonds while the PAN domain indicates protein-protein or protein-carbohydrate interactions (Vaid et al., 2013). Our annotation indicates that AT1G61550/G-LecRK-VI.13 has a S-domain, an EGF domain, a transmembrane domain and a kinase domain (FIG. 2).

Figure 3:
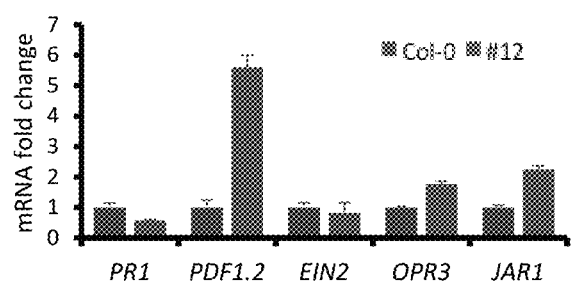
FIG. 3. Constitutive defense-related gene expression analysis using RT-qPCR in wild type *Arabidopsis* Col-0 and the AT1G61550/G-LecRK-VI.13 mutant line 12.

To characterize the underlying phenomenon of the enhanced RKN resistance in the AT1G61550/G-LecRK-VI.13 mutants, we investigated the constitutive expression of defense-related genes. Interestingly, three genes involved in jasmonic acid defense hormone, PDF1.2, JAR1 and OPR3 (as well as a camalexin biosynthesis gene PAD3 (data not shown)) are constitutively upregulated in mutant line 12 compared to wild type Col-0 (FIG. 3).

Figure 4:
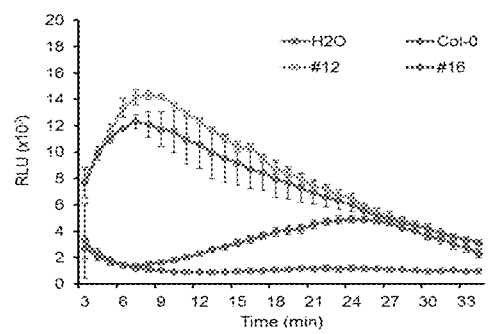
FIG. 4. ROS burst, over time (a) or cumulative (b), triggered by the flagellin-derived flg22 peptide in wild type Col-0 and AT1G61550/G-LecRK-VI.13 mutant lines 12 and 16. Col-0 treated with H20 was used as a negative control.
Figure 4:
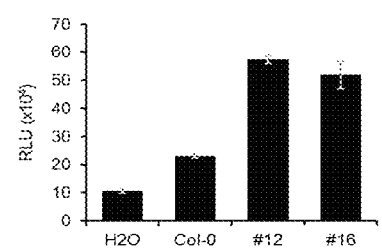
Figure 5:
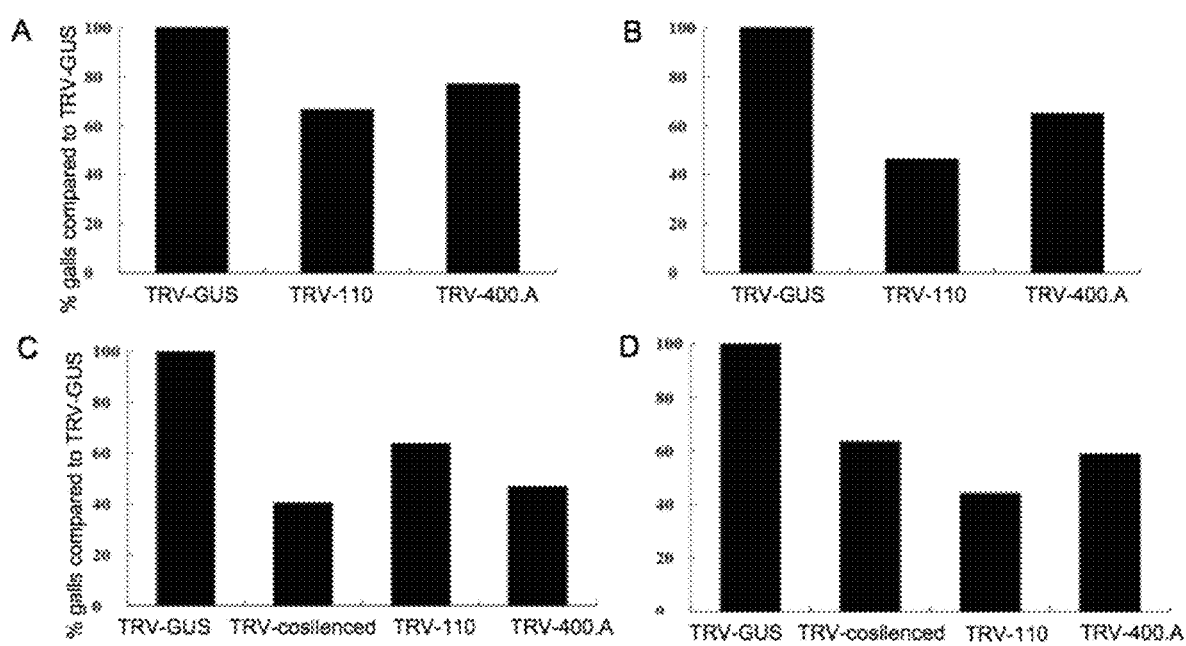
FIG. 5. Percentage galls compared to TRV-GUS control. TRV-110 silences Solyc04g058110; TRV-400.A silences Solyc04g008400.A; TRV-cosilenced silences both Solyc04g058110 and Solyc04g008400.A. Plants were infected with 500 infective-stage juveniles and evaluated 3 weeks after infection. Four independent experiments were performed (FIG. 5A-D). A, n=13; B, n=10; C, n=10; D, n=13.

To further confirm the enhanced immune response in the mutants lines, reactive oxygen species (ROS) burst, another hallmark for PTI activation, was assessed. ROS burst was induced in leaves with the flagellin-derived flg22 peptide, a potent elicitor of immunity, and quantified using chemiluminescense. Rapid and greatly enhanced ROS burst was detected in both mutant lines (12 and 16) compared to Col-0 (FIG. 4).

Identifying AT1G61550/G-LecRK-VI.13 Orthologs in Crops

We have used bioinformatics analysis to identify orthologs of AT1G61550/G-LecRK-VI.13 in rice (*Oryza sativa*), peanut (*Arachis duranensis*) and tomato (*Solanum lycopersicum*), all three crops considered good hosts for RKN. The top hits in rice (LOC_Os07g36590.1) and peanut, (Aradu.AX3Z0) are genes encoding identical motifs as AT1G61550/G-LecRK-VI.13 including the EGF motif.

We have identified two G-LecRK-VI.13 orthologs in tomato: Solyc04g058110 and Solyc04g008400.A. We used Tobacco rattle virus (TRV)-based virus-induced gene silencing (VIGS) (as described by Liu et al., 2002 *Plant J.* 31: 777-786) to silence these two genes either together or individually in tomato in four independent experiments (FIG. 5A-D). After transiently silencing these genes, individually or combined, we evaluated the plants with RKNs and measured the infection rate by counting the number of galls produced on the roots by the nematodes. For control, we used TRV-GUS construct. Individually silencing or co-silencing these two genes resulted in an average of 50% reduction in nematode infection rate, indicating they have non-redundant functions.

Considering that VIGS-based silencing is known to be patchy and not complete, particularly in roots (Jablonska et al. 2009 *Plant J.* 36: 905-917; Peng et al. 2014 *PLoS One* 9:e93302), and transcript levels are not completely eliminated but rather reduced (Liu et al. 2002; Ekengren et al. 2003 *Plant J.* 36: 905-917), the infection rates presented here are likely an overestimate. It is likely that knock-out of these two genes using other transgenic approaches (e.g. RNAi or CRISPR/Cas-9) will result in lower rates of RKN infection.

It is understood that the examples and embodiments described herein are for illustrative purposes only and that various modifications or changes in light thereof will be suggested to persons skilled in the art and are to be included within the spirit and purview of this application and scope of the appended claims. All publications, accession numbers, patents, and patent applications cited herein are hereby incorporated by reference in their entirety for all purposes.

What is claimed is:

1. A method of making a plant which has an enhanced immune response to root knot nematodes, the method comprising:
   a) introducing into a parent plant a recombinant construct that targets an endogenous G-LecRK-VI.13 gene and specifically inhibits activity in the plant of a G-LecRK-VI.13 polypeptide encoded by the gene, wherein the G-LecRK-VI.13 polypeptide has at least 95% amino acid sequence identity to SEQ ID NO:4 or SEQ ID NO:6; and
   b) selecting progeny of the parent plant having an enhanced immune response to root knot nematodes.

2. The method of claim 1, wherein the recombinant construct encodes a genome editing protein that specifically introduces mutations into the endogenous G-LecRK-VI.13 gene; and the step of selecting progeny comprises selecting progeny comprising a mutant of the endogenous G-LecRK-VI.13 gene and having an enhanced immune response to nematodes.

3. The method of claim 2, wherein the recombinant construct encodes an endonuclease and a guide RNA molecule that specifically targets the endonuclease to the endogenous G-LecRK-VI.13 gene.

4. The method of claim 3, wherein the endonuclease is Cas9.

5. The method of claim 1, wherein the recombinant construct encodes an RNA molecule that specifically inhibits expression of the endogenous G-LecRK-VI.13 gene.

6. The method of claim 5, wherein the expression cassette comprises a nucleic acid sequence encoding a microRNA or an siRNA specific to the endogenous G-LecRK-VI.13 gene.

7. The method of claim 1, wherein the endogenous G-LecRK-VI.13 gene is at least 90% identical to SEQ ID NO: 3 or 5.

8. The method of claim 1, wherein the G-LecRK-VI.13 polypeptide has at least 99% amino acid sequence identity to SEQ ID NO:4 or 6.

9. The method of claim 1, wherein the G-LecRK-VI.13 polypeptide comprises the amino acid sequence of SEQ ID NO:4 or 6.

10. The method of claim 9, wherein the plant is tomato.

11. A plant made by the method of claim 1.

12. A recombinant construct encoding a genome editing protein that specifically introduces mutations into a G-LecRK-VI.13 gene that is endogenous to a plant and encodes a G-LecRK-VI.13 polypeptide having at least 95% amino acid sequence identity to SEQ ID NO:4 or 6.

13. The recombinant construct of claim 12, wherein the recombinant construct encodes an endonuclease and a guide RNA molecule that specifically targets the endonuclease to the G-LecRK-VI.13 gene.

14. The recombinant construct of claim 13, wherein the endonuclease is Cas9.

15. The recombinant construct of claim 12, wherein the G-LecRK-VI.13 polypeptide has at least 99% amino acid sequence identity to SEQ ID NO:4 or 6.

16. The recombinant construct of claim 12, wherein the G-LecRK-VI.13 polypeptide comprises the amino acid sequence of SEQ ID NO:4 or 6.

17. A recombinant construct encoding an RNA transcript that specifically inhibits expression of a G-LecRK-VI.13 gene that is endogenous to a plant and encodes a G-LecRK-VI.13 polypeptide having at least 95% amino acid sequence identity to SEQ ID NO:4 or 6.

18. The recombinant construct of claim 17, wherein the RNA transcript is a microRNA or an siRNA.

19. The recombinant construct of claim 17, wherein the G-LecRK-VI.13 polypeptide has at least 99% amino acid sequence identity to SEQ ID NO:4 or SEQ ID NO:6.

20. The recombinant construct of claim 17, wherein the G-LecRK-VI.13 comprises the amino acid sequence of SEQ ID NO:4 or SEQ ID NO:6.

\* \* \* \* \*

SEQUENCE LISTING

```
<160> NUMBER OF SEQ ID NOS: 6

<210> SEQ ID NO 1
<211> LENGTH: 2982
<212> TYPE: DNA
<213> ORGANISM: Arabidopsis thaliana

<400> SEQUENCE: 1
atgacgaggt tgcttgctt tctcttctct accttgctct taagttttag ctatgcagct      60
ataacaccaa caagtccttt gtcaattgga caaactctca gctcccctaa tggaattttc     120
gaactggggt ttttcagtcc taataactct cggaatttgt atgttggaat ctggttcaag     180
ggtatcattc cccggacggt tgtgtgggtg gccaatagaa aaaattctgt tacagacgcc     240
actgcggatc tagctatcag tagcaatgga agtcttctct tatttgatgg caaacatagc     300
actgtctggt ccaccggaga aacttttgca tctaacgggt ctagtgcaga gctttcagac     360
agcggaaatc ttttggtcat agacaaagtt tcgggaataa ctctatggca aagctttgag     420
catcttggtg atactatgct accttactcc tccctgatgt ataaccccgg cactggtgag     480
aagcgggtat tgtcttcttg gaaaagttac actgatccat tgcctggtga gtttgtgggt     540
tatattacaa cacaagtgcc accacagggg tttattatga gaggctcgaa gccttattgg     600
agaagcggtc cttgggctaa aacaaggttt actggcgtac cactaacgga tgaatcatac     660
acacatccat ttagcgttca gcaagatgca aacgggtcag tatacttctc tcatttacaa     720
agaaacttca aacgttcatt gttagtatta acatcagagg ggtcactgaa ggttactcat     780
cataatggca cggactgggt attgaacatt gatgttccag ctaacacatg tgattttac     840 ggtgtatgtg gaccttttgg attgtgtgta atgtccattc ctccaaagtg taaatgcttt     900
aaaggctttg taccacaatt cagtgaggaa tggaaaagag gaaattggac tggtggttgt     960
gtgaggcgta ctgaactact ttgtcaagga aactctactg ggagacatgt aaacgtcttc    1020
catcctgttg ccaacataaa acctccagac ttttacgaat ttgtgtcctc cgggagtgca    1080
gaagaatgct accaaagttg cctccacaat tgttcatgct tggcctttgc ttatattaat    1140
ggaatagggt gcttaatttg gaaccaggag ctaatggatg taatgcaatt ctctgtggga    1200
ggagagcttc tttctatacg tcttgcaagt tctgaaatgg gtggaaacca gcgcaagaag    1260
accattattg ctagtattgt tagcatttct ctttttgtga cattggcttc tgctgcgttt    1320
ggtttctgga gatacagatt gaaacataat gcaattgtat cgaaggtttc tttacaaggt    1380
gcatggagga atgatttgaa atcagaagat gtctcaggtt tatatttctt tgagatgaag    1440
```

-continued

```
accattgaaa ttgccaccaa taatttcagt ctcgtaaaca aactcggaca aggtggattt    1500
ggtccagttt acaagggaaa gttacaagat gggaaagaaa tagctgtaaa acggctttcc    1560
agcagctctg gacagggaaa ggaggagttc atgaatgaaa tactactcat ctcaaaactc    1620
caacacataa acttggttcg gattttagga tgttgcattg aaggagaaga gcgactgttg    1680
gtttatgagt tcatggtgaa caaaagcctt gatactttta tctttgattc aagaaaaagg    1740
gttgagattg attggcctaa gaggttcagt attattcaag gaattgcgcg tggtcttctc    1800
tatctccacc gtgactcacg cctcaggata attcaccgag atgtgaaggt tagcaatatt    1860
cttcttgacg ataaaatgaa cccgaaaata tcagattttg gattggctcg gatgtatgaa    1920
ggaaccaaat atcaggacaa cactcgcagg attgtaggaa ctctaggata tatgtctcct    1980
gagtatgcat ggactggagt tttctctgag aagtccgaca cctacagctt tggagttctc    2040
ttgttagaag ttatcagcgg agagaagatc tcgaggttta gctatgataa agagcgcaaa    2100
aaccttcttg catatgcgtg ggaatcttgg tgcgaaaatg gaggagttgg ttttttggat    2160
aaagatgcta ctgattcatg tcacccatct gaagttggaa ggtgtgttca gattggtctg    2220
ctttgtgttc agcaccaacc tgctgataga cccaacacac ttgagttgtt gtctatgctc    2280
acaacaacat cagatcttcc actacctaaa gaacccacat ttgcagtgca tactagcgat    2340
gacggatccc gcactagtga tttgattaca gtcaatgagg tgacacaatc tgtggtgcta    2400
gggcgttaag aacaatgctt taccatagtt taaaatgatc taattttcag tgtttgtact    2460
ttgtaacttc aacatacatt cataatttac ttcattttc aaataaaggg gtttggcatt    2520
tttgctctgt tctcgctggt aacagtgaca cacgccaatg ttacataatg taacttacat    2580
tagacacaca aacagtgaca ttaatgtaaa gagaaccgta gccttctaat ttatgcaaca    2640
caacaaaagt gtattcaaat acattttgta agaggaagca aaacaatgcc aattgcattc    2700
gctaaaaccg taaccaaat attcatcata ggaacatact aatcaaaaca aaatgacatt    2760
atccgcgtta accattcaag ccatcaaaga gtagcagaaa gaccatccgc atacaacaaa    2820
cgacaagact tgtggactgg aagcacagca tcaaaccact caactttccc ccaaatctca    2880
tctccatcac cacgcctttc aagcgaaatc tccgcacacc aaatcacatt ctctttacgt    2940
ctacttgaat aatacacaga cgcatcccac aacaccatca tc                      2982
```

<210> SEQ ID NO 2
<211> LENGTH: 802
<212> TYPE: PRT
<213> ORGANISM: Arabidopsis thaliana

<400> SEQUENCE: 2

```
Met Thr Arg Phe Ala Cys Phe Leu Phe Ser Thr Leu Leu Ser Phe
1               5                   10                  15

Ser Tyr Ala Ala Ile Thr Pro Thr Ser Pro Leu Ser Ile Gly Gln Thr
                20                  25                  30

Leu Ser Ser Pro Asn Gly Ile Phe Glu Leu Gly Phe Phe Ser Pro Asn
            35                  40                  45

Asn Ser Arg Asn Leu Tyr Val Gly Ile Trp Phe Lys Gly Ile Ile Pro
        50                  55                  60

Arg Thr Val Val Trp Val Ala Asn Arg Glu Asn Ser Val Thr Asp Ala
65                  70                  75                  80

Thr Ala Asp Leu Ala Ile Ser Ser Asn Gly Ser Leu Leu Leu Phe Asp
                85                  90                  95
```

-continued

Gly Lys His Ser Thr Val Trp Ser Thr Gly Glu Thr Phe Ala Ser Asn
            100                 105                 110

Gly Ser Ser Ala Glu Leu Ser Asp Ser Gly Asn Leu Leu Val Ile Asp
            115                 120                 125

Lys Val Ser Gly Ile Thr Leu Trp Gln Ser Phe Glu His Leu Gly Asp
            130                 135                 140

Thr Met Leu Pro Tyr Ser Ser Leu Met Tyr Asn Pro Gly Thr Gly Glu
145                 150                 155                 160

Lys Arg Val Leu Ser Ser Trp Lys Ser Tyr Thr Asp Pro Leu Pro Gly
                165                 170                 175

Glu Phe Val Gly Tyr Ile Thr Thr Gln Val Pro Pro Gln Gly Phe Ile
            180                 185                 190

Met Arg Gly Ser Lys Pro Tyr Trp Arg Ser Gly Pro Trp Ala Lys Thr
            195                 200                 205

Arg Phe Thr Gly Val Pro Leu Thr Asp Glu Ser Tyr Thr His Pro Phe
            210                 215                 220

Ser Val Gln Gln Asp Ala Asn Gly Ser Val Tyr Phe Ser His Leu Gln
225                 230                 235                 240

Arg Asn Phe Lys Arg Ser Leu Leu Val Leu Thr Ser Glu Gly Ser Leu
                245                 250                 255

Lys Val Thr His His Asn Gly Thr Asp Trp Val Leu Asn Ile Asp Val
            260                 265                 270

Pro Ala Asn Thr Cys Asp Phe Tyr Gly Val Cys Gly Pro Phe Gly Leu
            275                 280                 285

Cys Val Met Ser Ile Pro Pro Lys Cys Lys Cys Phe Lys Gly Phe Val
            290                 295                 300

Pro Gln Phe Ser Glu Glu Trp Lys Arg Gly Asn Trp Thr Gly Gly Cys
305                 310                 315                 320

Val Arg Arg Thr Glu Leu Leu Cys Gln Gly Asn Ser Thr Gly Arg His
                325                 330                 335

Val Asn Val Phe His Pro Val Ala Asn Ile Lys Pro Pro Asp Phe Tyr
            340                 345                 350

Glu Phe Val Ser Ser Gly Ser Ala Glu Glu Cys Tyr Gln Ser Cys Leu
            355                 360                 365

His Asn Cys Ser Cys Leu Ala Phe Ala Tyr Ile Asn Gly Ile Gly Cys
            370                 375                 380

Leu Ile Trp Asn Gln Glu Leu Met Asp Val Met Gln Phe Ser Val Gly
385                 390                 395                 400

Gly Glu Leu Leu Ser Ile Arg Leu Ala Ser Ser Glu Met Gly Gly Asn
                405                 410                 415

Gln Arg Lys Lys Thr Ile Ile Ala Ser Ile Val Ser Ile Ser Leu Phe
            420                 425                 430

Val Thr Leu Ala Ser Ala Ala Phe Gly Phe Trp Arg Tyr Arg Leu Lys
            435                 440                 445

His Asn Ala Ile Val Ser Lys Val Ser Leu Gln Gly Ala Trp Arg Asn
            450                 455                 460

Asp Leu Lys Ser Glu Asp Val Ser Gly Leu Tyr Phe Phe Glu Met Lys
465                 470                 475                 480

Thr Ile Glu Ile Ala Thr Asn Asn Phe Ser Leu Val Asn Lys Leu Gly
                485                 490                 495

Gln Gly Gly Phe Gly Pro Val Tyr Lys Gly Lys Leu Gln Asp Gly Lys
            500                 505                 510

Glu Ile Ala Val Lys Arg Leu Ser Ser Ser Ser Gly Gln Gly Lys Glu

```
            515                 520                 525
Glu Phe Met Asn Glu Ile Leu Leu Ile Ser Lys Leu Gln His Ile Asn
            530                 535                 540
Leu Val Arg Ile Leu Gly Cys Cys Ile Glu Gly Glu Arg Leu Leu
545                 550                 555                 560
Val Tyr Glu Phe Met Val Asn Lys Ser Leu Asp Thr Phe Ile Phe Asp
                565                 570                 575
Ser Arg Lys Arg Val Glu Ile Asp Trp Pro Lys Arg Phe Ser Ile Ile
            580                 585                 590
Gln Gly Ile Ala Arg Gly Leu Leu Tyr Leu His Arg Asp Ser Arg Leu
            595                 600                 605
Arg Ile Ile His Arg Asp Val Lys Val Ser Asn Ile Leu Leu Asp Asp
610                 615                 620
Lys Met Asn Pro Lys Ile Ser Asp Phe Gly Leu Ala Arg Met Tyr Glu
625                 630                 635                 640
Gly Thr Lys Tyr Gln Asp Asn Thr Arg Arg Ile Val Gly Thr Leu Gly
                645                 650                 655
Tyr Met Ser Pro Glu Tyr Ala Trp Thr Gly Val Phe Ser Glu Lys Ser
                660                 665                 670
Asp Thr Tyr Ser Phe Gly Val Leu Leu Glu Val Ile Ser Gly Glu
            675                 680                 685
Lys Ile Ser Arg Phe Ser Tyr Asp Lys Glu Arg Lys Asn Leu Leu Ala
            690                 695                 700
Tyr Ala Trp Glu Ser Trp Cys Glu Asn Gly Val Gly Phe Leu Asp
705                 710                 715                 720
Lys Asp Ala Thr Asp Ser Cys His Pro Ser Glu Val Gly Arg Cys Val
                725                 730                 735
Gln Ile Gly Leu Leu Cys Val Gln His Gln Pro Ala Asp Arg Pro Asn
                740                 745                 750
Thr Leu Glu Leu Leu Ser Met Leu Thr Thr Thr Ser Asp Leu Pro Leu
            755                 760                 765
Pro Lys Glu Pro Thr Phe Ala Val His Thr Ser Asp Asp Gly Ser Arg
            770                 775                 780
Thr Ser Asp Leu Ile Thr Val Asn Glu Val Thr Gln Ser Val Val Leu
785                 790                 795                 800
Gly Arg

<210> SEQ ID NO 3
<211> LENGTH: 2466
<212> TYPE: DNA
<213> ORGANISM: Solanum lycopersicum

<400> SEQUENCE: 3
atgagcaaca gcagcagcag aagaaatttg caatatttg ttcatataat tcttgttatt      60
cttcgttttg tcgatacagg attatgcagt gaagtggata acattactag cattcagtct     120
ctgagagatc ctggaatttt atcgtctcca ggaggcgtat tcaagttagg attttcagt     180 cctcaaaaca gtagtaatag gtatgttggt atttggtaca ttttttctgt aacaacagtc     240
atttgggtgg ctaatcgaga caaacccttta agagattctt ctggagttgt gaagatatct     300
cgtgatggaa atatcgttat aacgaatgga gaggaggaga ttcttggtc atcaaatgtt     360 tcaacttctc aggtgatcat cccaattgga cttctccaag attctggcaa ctttgttctc     420
gttgatcatc gggacatgag cacaatatgg cagagttttg aacatccttc tgattcaact     480
```

| | | | | |
|---|---|---|---|---|
| attcctagaa | tgagaataag | tgaaaacaca | aggacagggg | agatggtaga agcaacatct | 540 |
| tggagaagtc | cttcggatcc | taatatcggg | gacttttctt | taagaatgaa ctctggagtc | 600 |
| attcctcagg | tgtatatatg | gaaaggaagg | cgtccctatt | ggcgtactgg tcaatggaat | 660 |
| ggacagatct | ttataggagt | gcagaatatg | tattctgtgg | tgtctgatgg atttaatgta | 720 |
| gtggatgatc | gcgaaggtac | tgtatatttt | actggaccta | ctcgtgataa ttttttaagg | 780 |
| atattagtct | tggattggag | agggaacttg | gttcaatcat | attgggatgt gaatgagaca | 840 |
| aaatggaaga | taatatggtc | agctcccaat | aacgattgtg | aagtttatgg aacgtgtggt | 900 |
| ccatttggga | gctgcaatca | cttggagtca | ccagtctgtt | cttgtctgaa aggttttgag | 960 |
| ccaaagcaca | tggaagaatg | ggaaaagggg | aattggacta | gtggttgtgt taggaggagt | 1020 |
| gctttgcaat | gtgaagttaa | gaataacacc | acggattcaa | gtaaagaaga cggatttcta | 1080 |
| aagatggagt | taatgaaatt | gcctgatttt | gctgaaaggt | catctactac agaagacgta | 1140 |
| tgtagaagtc | gatgcttggg | gaattgttcg | tgcatagggt | atgcatttga ttcaagtatc | 1200 |
| ggctgtatgt | cgtggagtat | aatgattgac | attcagcagt | tccaaagctc ggggaaagat | 1260 |
| ctctatattc | atgtagcaca | ttcagagctt | gtgttttctg | cagatcatcg taaagagtac | 1320 |
| ataaagaaaa | tcgtaattcc | agtaatcgtt | ggttctctta | cactctgtgt ttgtctgttc | 1380 |
| ctttgctata | caatgatggt | cagacgtaga | ggagtgaaaa | gagaggaggt tttacttggt | 1440 |
| aacaaaagtc | cagttaatat | ggaagaatta | ccagtcttca | gcctcgatac gcttgtaaat | 1500 |
| gcaacatccc | aattcaatga | ggataataag | cttggtcagg | gaggttttgg tccagtttac | 1560 |
| aagggaatat | tggaagatgg | gaaagaaatt | gctgtcaaga | ggctctcaaa agcctcgaaa | 1620 |
| caaggactag | aggagttcat | gaatgaagtg | ttggtgatct | cgaaagttca acatagaaac | 1680 |
| cttgttagac | tctgtggatg | ttgtgtcgat | gaagaggaga | agatgctaat ttacgaatat | 1740 |
| atgccaaaga | aaagcttaga | tgtgtttctc | tttgatgaag | gacatcgaga catattggat | 1800 |
| tggacaaaac | gttccattat | aatcgaagga | gttggtcgag | gactcccttta tcttcacaga | 1860 |
| gattcaagat | tgaagataat | ccatagagat | ctaaagccaa | gtaacatctt gctcgataat | 1920 |
| aacttcaatc | caaagatctc | agattttggc | atggctagga | ttttcggatc tgatcaagat | 1980 |
| caagcagaca | caatgagagt | agttggtact | tatggataca | tggcacccga atatgcaatg | 2040 |
| gaaggaagat | tctcagagaa | atccgatgtt | ttcagctttg | gagttctcgt cttagagatc | 2100 |
| ataagtggtc | gaaaaagtac | aagttcttgg | actgagacat | cctcttttgag ccttatggga | 2160 |
| tatgcatgga | agttatggaa | agaacaagat | ttatcaactt | tcatcgatcc gtttatattg | 2220 |
| aacacgagct | cggaaatgga | gatcagaaaa | tgcatacaga | ttggtttatt gtgtgttcaa | 2280 |
| gaatttgctg | aagacaggcc | aaatatttca | tctgttcttg | ttatgcttac tagtgaaaca | 2340 |
| acaagtcttc | cagcaccatc | acaacctgct | tttactgaaa | gaagacactt cagaatgtgc | 2400 |
| aatgaaaata | gagaaactaa | gtttactttg | aacaaaatga | gtatcacaaa ccttactggt | 2460 |
| agataa | | | | | 2466 |

<210> SEQ ID NO 4
<211> LENGTH: 820
<212> TYPE: PRT
<213> ORGANISM: Solanum lycopersicum

<400> SEQUENCE: 4

Met Ser Asn Ser Ser Ser Arg Arg Asn Leu Gln Tyr Phe Val His Ile
1               5                   10                  15

```
Ile Leu Val Ile Leu Arg Phe Val Asp Thr Gly Leu Cys Ser Glu Val
                20                  25                  30

Asp Asn Ile Thr Ser Ile Gln Ser Leu Arg Asp Pro Gly Ile Leu Ser
         35                  40                  45

Ser Pro Gly Gly Val Phe Lys Leu Gly Phe Phe Ser Pro Gln Asn Ser
 50                  55                  60

Ser Asn Arg Tyr Val Gly Ile Trp Tyr Asn Phe Ser Val Thr Thr Val
65                   70                  75                  80

Ile Trp Val Ala Asn Arg Asp Lys Pro Leu Arg Asp Ser Ser Gly Val
                85                  90                  95

Val Lys Ile Ser Arg Asp Gly Asn Ile Val Ile Thr Asn Gly Glu Glu
                100                 105                 110

Glu Ile Leu Trp Ser Ser Asn Val Ser Thr Ser Gln Val Ile Ile Pro
        115                 120                 125

Ile Gly Leu Leu Gln Asp Ser Gly Asn Phe Val Leu Val Asp His Arg
        130                 135                 140

Asp Met Ser Thr Ile Trp Gln Ser Phe Glu His Pro Ser Asp Ser Thr
145                 150                 155                 160

Ile Pro Arg Met Arg Ile Ser Glu Asn Thr Arg Thr Gly Glu Met Val
                165                 170                 175

Glu Ala Thr Ser Trp Arg Ser Pro Ser Asp Pro Asn Ile Gly Asp Phe
            180                 185                 190

Ser Leu Arg Met Asn Ser Gly Val Ile Pro Gln Val Tyr Ile Trp Lys
            195                 200                 205

Gly Arg Arg Pro Tyr Trp Arg Thr Gly Gln Trp Asn Gly Gln Ile Phe
210                 215                 220

Ile Gly Val Gln Asn Met Tyr Ser Val Val Ser Asp Gly Phe Asn Val
225                 230                 235                 240

Val Asp Asp Arg Glu Gly Thr Val Tyr Phe Thr Gly Pro Thr Arg Asp
                245                 250                 255

Asn Phe Leu Arg Ile Leu Val Leu Asp Trp Arg Gly Asn Leu Val Gln
            260                 265                 270

Ser Tyr Trp Asp Val Asn Glu Thr Lys Trp Lys Ile Ile Trp Ser Ala
    275                 280                 285

Pro Asn Asn Asp Cys Glu Val Tyr Gly Thr Cys Gly Pro Phe Gly Ser
    290                 295                 300

Cys Asn His Leu Glu Ser Pro Val Cys Ser Cys Leu Lys Gly Phe Glu
305                 310                 315                 320

Pro Lys His Met Glu Gly Trp Glu Lys Gly Asn Trp Thr Ser Gly Cys
                325                 330                 335

Val Arg Arg Ser Ala Leu Gln Cys Glu Val Lys Asn Asn Thr Thr Asp
            340                 345                 350

Ser Ser Lys Glu Asp Gly Phe Leu Lys Met Glu Leu Met Lys Leu Pro
    355                 360                 365

Asp Phe Ala Glu Arg Ser Ser Thr Thr Glu Asp Val Cys Arg Ser Arg
    370                 375                 380

Cys Leu Gly Asn Cys Ser Cys Ile Gly Tyr Ala Phe Asp Ser Ser Ile
385                 390                 395                 400

Gly Cys Met Ser Trp Ser Ile Met Ile Asp Ile Gln Gln Phe Gln Ser
                405                 410                 415

Ser Gly Lys Asp Leu Tyr Ile His Val Ala His Ser Glu Leu Val Phe
            420                 425                 430

Ser Ala Asp His Arg Lys Glu Tyr Ile Lys Lys Ile Val Ile Pro Val
```

```
                435                 440                 445
Ile Val Gly Ser Leu Thr Leu Cys Val Cys Leu Phe Leu Cys Tyr Thr
450                 455                 460

Met Met Val Arg Arg Gly Val Lys Arg Glu Glu Val Leu Leu Gly
465                 470                 475                 480

Asn Lys Ser Pro Val Asn Met Glu Glu Leu Pro Val Phe Ser Leu Asp
                485                 490                 495

Thr Leu Val Asn Ala Thr Ser Gln Phe Asn Glu Asp Asn Lys Leu Gly
            500                 505                 510

Gln Gly Gly Phe Gly Pro Val Tyr Lys Gly Ile Leu Glu Asp Gly Lys
        515                 520                 525

Glu Ile Ala Val Lys Arg Leu Ser Lys Ala Ser Lys Gln Gly Leu Glu
    530                 535                 540

Glu Phe Met Asn Glu Val Leu Val Ile Ser Lys Val Gln His Arg Asn
545                 550                 555                 560

Leu Val Arg Leu Cys Gly Cys Cys Val Asp Glu Glu Glu Lys Met Leu
                565                 570                 575

Ile Tyr Glu Tyr Met Pro Lys Lys Ser Leu Asp Val Phe Leu Phe Asp
            580                 585                 590

Glu Gly His Arg Asp Ile Leu Asp Trp Thr Lys Arg Ser Ile Ile Ile
        595                 600                 605

Glu Gly Val Gly Arg Gly Leu Leu Tyr Leu His Arg Asp Ser Arg Leu
    610                 615                 620

Lys Ile His Arg Asp Leu Lys Pro Ser Asn Ile Leu Leu Asp Asn
625                 630                 635                 640

Asn Phe Asn Pro Lys Ile Ser Asp Phe Gly Met Ala Arg Ile Phe Gly
                645                 650                 655

Ser Asp Gln Asp Gln Ala Asp Thr Met Arg Val Val Gly Thr Tyr Gly
            660                 665                 670

Tyr Met Ala Pro Glu Tyr Ala Met Glu Gly Arg Phe Ser Glu Lys Ser
        675                 680                 685

Asp Val Phe Ser Phe Gly Val Leu Val Leu Glu Ile Ile Ser Gly Arg
    690                 695                 700

Lys Ser Thr Ser Ser Trp Thr Glu Thr Ser Ser Leu Ser Leu Met Gly
705                 710                 715                 720

Tyr Ala Trp Lys Leu Trp Lys Glu Gln Asp Leu Ser Thr Phe Ile Asp
                725                 730                 735

Pro Phe Ile Leu Asn Thr Ser Ser Glu Met Glu Ile Arg Lys Cys Ile
            740                 745                 750

Gln Ile Gly Leu Leu Cys Val Gln Glu Phe Ala Glu Asp Arg Pro Asn
        755                 760                 765

Ile Ser Ser Val Leu Val Met Leu Thr Ser Glu Thr Thr Ser Leu Pro
    770                 775                 780

Ala Pro Ser Gln Pro Ala Phe Thr Glu Arg Arg His Phe Arg Met Cys
785                 790                 795                 800

Asn Glu Asn Arg Glu Thr Lys Phe Thr Leu Asn Lys Met Ser Ile Thr
                805                 810                 815

Asn Leu Thr Gly
            820

<210> SEQ ID NO 5
<211> LENGTH: 2448
<212> TYPE: DNA
<213> ORGANISM: Solanum lycopersicum
```

<400> SEQUENCE: 5

```
atgaccacca ccagcagaaa tgtgcaacat tttgttcatg taattcttgt ttttcttcat     60
tgttttaata caggattttg cacagaaata gatagcatta ccagcactct atctctgagg    120
gatcctggga ttttatcatc tccaggaggc gtcttgaagt tgggattttt cagtcctcta    180
aacagctcta acaggtatgt tggtatttgg tacaattttt ctgaaacaat tgtcatttgg    240
gtggctaata gggacaaacc tttaagagat tcttctgggg ttgtgaagat ttctggtgat    300
ggaaatgtcg tcgttatgaa tggggaggag gagattcttt ggtcatcaaa tgtttcaacc    360
tctcaggtaa actcaattgc ccttctccaa gattctggga actttgttct tgtagatcat    420
ctgaataatg ggagcacaat atggcagagt tttgaacatc cttctgattc aattgtccct    480
aaaatgagta taagtgaaaa cacaaggaca ggggagaggg tagaagtaaa atcttggaga    540
agcccttggg atcctaattt cggaaacttt tctctaggaa tgaattctgg attcattcct    600
caggtgtata tctggaaagg tagtcagccc tattggcgaa gtggtcaatg gaatggccag    660
atctttatcg gagtgcagga tatgtattct gtgtcgtctg atggattcaa tgtagtgaac    720
aatcgggaag gtactgtata tcttactggc cctggtgatt ttgatttctt aacgaaattt    780
gtcttggatt ggaaagggaa cttggttcaa tcatattggg atgcgaatga gacgacctgg    840
aagataatat ggtcagctcc caataacgat tgtgaagttt atggaatgtg tggtccattt    900
ggtagctgca atcatttgga gtcgccgatt tgttcttgtc tgaaaggttt cgagccaaag    960
cacagggaag aatgggaaaa ggggaattgg gttagtggtt gtcttaggag gaaagctttg   1020
caatgtgaag taaggaataa ctcaggggat tcaagtaaag aagacggatt tctaaagata   1080
gggtcaataa aattgcctga tttttcagaa aggtcatcga ctagagaaga ccagtgtaga   1140
agccaatgtt tgggaaattg ttcctgcata gcgtatgcat atgactcagg tattggctgt   1200
atgtcgtgga ataacaactt gattgatatt cagcagttcc aaagcagggg ggaagatctc   1260
tatattcgca tggcacattc agagcttgat catcataaag acataaagaa aattgtaatt   1320
ccagtaatcc ttggttttct tacactctgt gtttgtctgt tcctttgttg tacaagaatg   1380
gccagacgta gaggagtaaa aaggaagaag ataaatttac ttggtgacag aagtgcagtt   1440
catatggaag agttaccagt cttcagcctc gatacacttg caaatgcaac atcccagttc   1500
catgaggata agaagcttgg tcagggtggt tttggtccag tttacatggg aaaattggaa   1560
gatgggaaag aaatagcagt caagaagctt tcaaaagcct cgggacaagg gctggaggag   1620
ttcatgaatg aagtgttggt gatctctaaa gtccaacata gaaaccttgt tagactcttg   1680
ggatgttgcg ttgataaaga ggagaagatg ttgatttatg aatatatgcc caagaaaagc   1740
ttggatgtgt ttctctttga tgaaggacac cgaggcattt tggattggag aaaatgttcc   1800
actataatcg aaggggttgg tcgaggactc ctttatcttc acagagattc aagattgaag   1860
ataattcata gagatctgaa gccaagtaac attttgctcg ataatgactt caatccaaag   1920
atttcagatt ttggcatggc taggattttc gggtctgacc aagatcaagc agacacaagg   1980
agagtagttg gtacttatgg atacatggct ccagaatatg caatgaaagg aagattctct   2040
gagaaatccg acgtcttcag ctttggagtt ctagtgttag agatcatcag tggccgaaaa   2100
agtacaagtt cttggaatga gacatcctct tttagccttt tcggatatgc atggatgtta   2160
tggaaagaac aagattatc  aactttatc  gatccattca  tattgaatcc  gagctcagaa   2220
atggagataa aaaaatgcat acagattggt ttactatgcg ttcaagaatt tgctgaagac   2280
```

```
aggccaagta tttcatcagt tcttgctatg cttaccagtg aaactacaag tattcctaca    2340
ccatcacaac ctgctttta c tgaaagacat gattgtatct tcaaaatgtg caatgaaact    2400
aattgtactt tgaacaatat cagtatcaca aacataactg gtagatga                 2448
```

<210> SEQ ID NO 6
<211> LENGTH: 795
<212> TYPE: PRT
<213> ORGANISM: Solanum lycopersicum

<400> SEQUENCE: 6

```
Met Thr Thr Thr Ser Arg Asn Val Gln His Phe Val His Val Ile Leu
1               5                   10                  15

Val Phe Leu His Cys Phe Asn Thr Gly Phe Cys Thr Glu Ile Asp Ser
            20                  25                  30

Ile Thr Ser Thr Leu Ser Leu Arg Asp Pro Gly Ile Leu Ser Ser Pro
        35                  40                  45

Gly Gly Val Leu Lys Leu Gly Phe Phe Ser Pro Leu Asn Ser Ser Asn
    50                  55                  60

Arg Asp Lys Pro Leu Arg Asp Ser Ser Gly Val Val Lys Ile Ser Gly
65                  70                  75                  80

Asp Gly Asn Val Val Met Asn Gly Glu Glu Ile Leu Trp Ser
                85                  90                  95

Ser Asn Val Ser Thr Ser Gln Val Asn Ser Ile Ala Leu Leu Gln Asp
            100                 105                 110

Ser Gly Asn Phe Val Leu Val Asp His Leu Asn Asn Gly Ser Thr Ile
        115                 120                 125

Trp Gln Ser Phe Glu His Pro Ser Asp Ser Ile Val Pro Lys Met Ser
    130                 135                 140

Ile Ser Glu Asn Thr Arg Thr Gly Glu Arg Val Glu Val Lys Ser Trp
145                 150                 155                 160

Arg Ser Pro Trp Asp Pro Asn Phe Gly Asn Phe Ser Leu Gly Met Asn
                165                 170                 175

Ser Gly Phe Ile Pro Gln Val Tyr Ile Trp Lys Gly Ser Gln Pro Tyr
            180                 185                 190

Trp Arg Ser Gly Gln Trp Asn Gly Gln Ile Phe Ile Gly Val Gln Asp
        195                 200                 205

Met Tyr Ser Val Ser Ser Asp Gly Phe Asn Val Asn Asn Arg Glu
    210                 215                 220

Gly Thr Val Tyr Leu Thr Gly Pro Gly Asp Phe Asp Phe Leu Thr Lys
225                 230                 235                 240

Phe Val Leu Asp Trp Lys Gly Asn Leu Val Gln Ser Tyr Trp Asp Ala
                245                 250                 255

Asn Glu Thr Thr Trp Lys Ile Ile Trp Ser Ala Pro Asn Asn Asp Cys
            260                 265                 270

Glu Val Tyr Gly Met Cys Gly Pro Phe Gly Ser Cys Asn His Leu Glu
        275                 280                 285

Ser Pro Ile Cys Ser Cys Leu Lys Gly Phe Glu Pro Lys His Arg Glu
    290                 295                 300

Glu Trp Glu Lys Gly Asn Trp Val Ser Gly Cys Leu Arg Arg Lys Ala
305                 310                 315                 320

Leu Gln Cys Glu Val Arg Asn Asn Ser Gly Asp Ser Ser Lys Glu Asp
                325                 330                 335

Gly Phe Leu Lys Ile Gly Ser Ile Lys Leu Pro Asp Phe Ser Glu Arg
            340                 345                 350
```

```
Ser Ser Thr Arg Glu Asp Gln Cys Arg Ser Gln Cys Leu Gly Asn Cys
        355                 360                 365

Ser Cys Ile Ala Tyr Ala Tyr Asp Ser Gly Ile Gly Cys Met Ser Trp
    370                 375                 380

Asn Asn Asn Leu Ile Asp Ile Gln Gln Phe Gln Ser Arg Gly Glu Asp
385                 390                 395                 400

Leu Tyr Ile Arg Met Ala His Ser Glu Leu Asp His His Lys Asp Ile
                405                 410                 415

Lys Lys Ile Val Ile Pro Val Ile Leu Gly Phe Leu Thr Leu Cys Val
                420                 425                 430

Cys Leu Phe Leu Cys Cys Thr Arg Met Ala Arg Arg Gly Val Lys
            435                 440                 445

Arg Lys Lys Ile Asn Leu Leu Gly Asp Arg Ser Ala Val His Met Glu
        450                 455                 460

Glu Leu Pro Val Phe Ser Leu Asp Thr Leu Ala Asn Ala Thr Ser Gln
465                 470                 475                 480

Phe His Glu Asp Lys Lys Leu Gly Gln Gly Gly Phe Gly Pro Val Tyr
                485                 490                 495

Met Gly Lys Leu Glu Asp Gly Lys Glu Ile Ala Val Lys Lys Leu Ser
                500                 505                 510

Lys Ala Ser Gly Gln Gly Leu Glu Glu Phe Met Asn Glu Val Leu Val
            515                 520                 525

Ile Ser Lys Val Gln His Arg Asn Leu Val Arg Leu Leu Gly Cys Cys
            530                 535                 540

Val Asp Lys Glu Glu Lys Met Leu Ile Tyr Glu Tyr Met Pro Lys Lys
545                 550                 555                 560

Ser Leu Asp Val Phe Leu Phe Asp Glu Gly His Arg Gly Ile Leu Asp
                565                 570                 575

Trp Arg Lys Cys Ser Thr Ile Ile Glu Gly Val Gly Arg Gly Leu Leu
            580                 585                 590

Tyr Leu His Arg Asp Ser Arg Leu Lys Ile Ile His Arg Asp Leu Lys
        595                 600                 605

Pro Ser Asn Ile Leu Leu Asp Asn Asp Phe Asn Pro Lys Ile Ser Asp
        610                 615                 620

Phe Gly Met Ala Arg Ile Phe Gly Ser Asp Gln Asp Gln Ala Asp Thr
625                 630                 635                 640

Arg Arg Val Val Gly Thr Tyr Gly Tyr Met Ala Pro Glu Tyr Ala Met
                645                 650                 655

Lys Gly Arg Phe Ser Glu Lys Ser Asp Val Phe Ser Phe Gly Val Leu
            660                 665                 670

Val Leu Glu Ile Ile Ser Gly Arg Lys Ser Thr Ser Ser Trp Asn Glu
            675                 680                 685

Thr Ser Ser Phe Ser Leu Phe Gly Tyr Ala Trp Met Leu Trp Lys Glu
        690                 695                 700

Gln Asp Leu Ser Thr Phe Ile Asp Pro Phe Ile Leu Asn Pro Ser Ser
705                 710                 715                 720

Glu Met Glu Ile Lys Lys Cys Ile Gln Ile Gly Leu Leu Cys Val Gln
                725                 730                 735

Glu Phe Ala Glu Asp Arg Pro Ser Ile Ser Ser Val Leu Ala Met Leu
            740                 745                 750

Thr Ser Glu Thr Thr Ser Ile Pro Thr Pro Ser Gln Pro Ala Phe Thr
        755                 760                 765
```

-continued

```
Glu Arg His Asp Cys Ile Phe Lys Met Cys Asn Glu Thr Asn Cys Thr
    770                 775                 780

Leu Asn Asn Ile Ser Ile Thr Asn Ile Thr Gly
785                 790                 795
```